United States Patent [19]

Hayashi et al.

[11] Patent Number: 5,048,960

[45] Date of Patent: Sep. 17, 1991

[54] MICROSPECTROSCOPE

[75] Inventors: Takahisa Hayashi; Nariaki Fujiwara, both of Kyoto, Japan

[73] Assignee: Dainippon Screen Mfg Co., Ltd, Japan

[21] Appl. No.: 361,406

[22] Filed: Jun. 5, 1989

[30] Foreign Application Priority Data

Jun. 8, 1988 [JP] Japan ................................. 63-140733

[51] Int. Cl.$^5$ .......................... G01J 3/42; G01B 11/86
[52] U.S. Cl. ..................................... 356/319; 356/381
[58] Field of Search ............... 356/319, 323, 325, 326, 356/328, 445, 446, 416, 381, 382

[56] References Cited

U.S. PATENT DOCUMENTS 4,802,763  2/1989  Gerlinger et al. ................. 356/446
4,844,617  7/1989  Kelderman et al. ................ 556/381

OTHER PUBLICATIONS

European Patent Application-82110785.1-Kishner et al.

Primary Examiner—Vincent P. McGraw
Assistant Examiner—LaCharles P. Keesee
Attorney, Agent, or Firm—Ostrolenk, Faber, Gerb & Soffen

[57] ABSTRACT

A method of and an apparatus for obtaining spectral data and calculating corrected spectral data. The method includes the steps of: obtaining spectral data $S'(\lambda)$ which is representative of the spectral characteristics of light which is generated by a light source and reflected by an object; substantially concurrently with the step of obtaining the spectral data $S'(\lambda)$, obtaining spectral data $R(\lambda)$ which is representative of the spectral characteristics of light which is generated by the light source; and calculating corrected spectral data $S(\lambda)$ as a function of the spectral data $S'(\lambda)$ and the spectral data $R(\lambda)$.

6 Claims, 13 Drawing Sheets

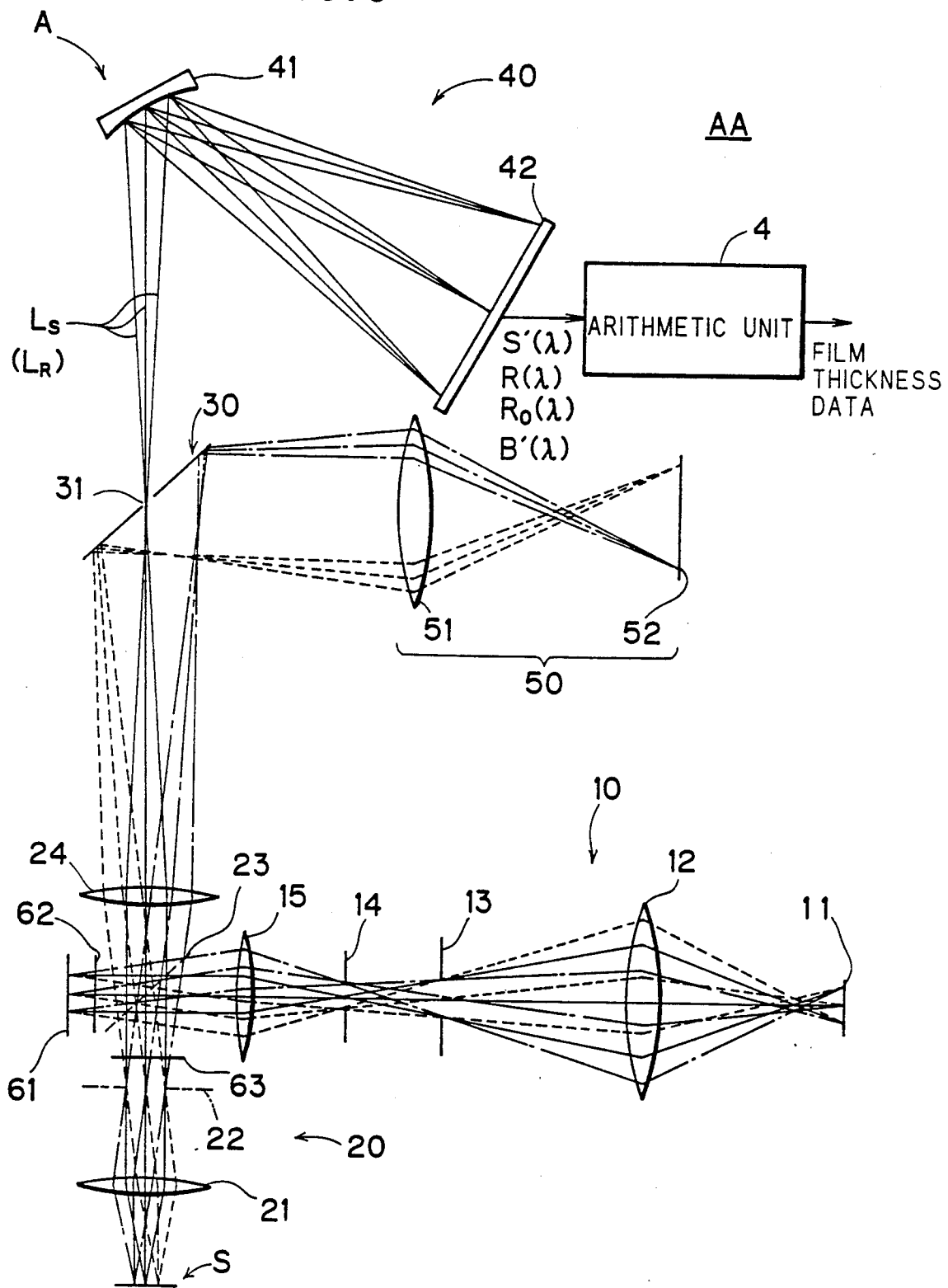

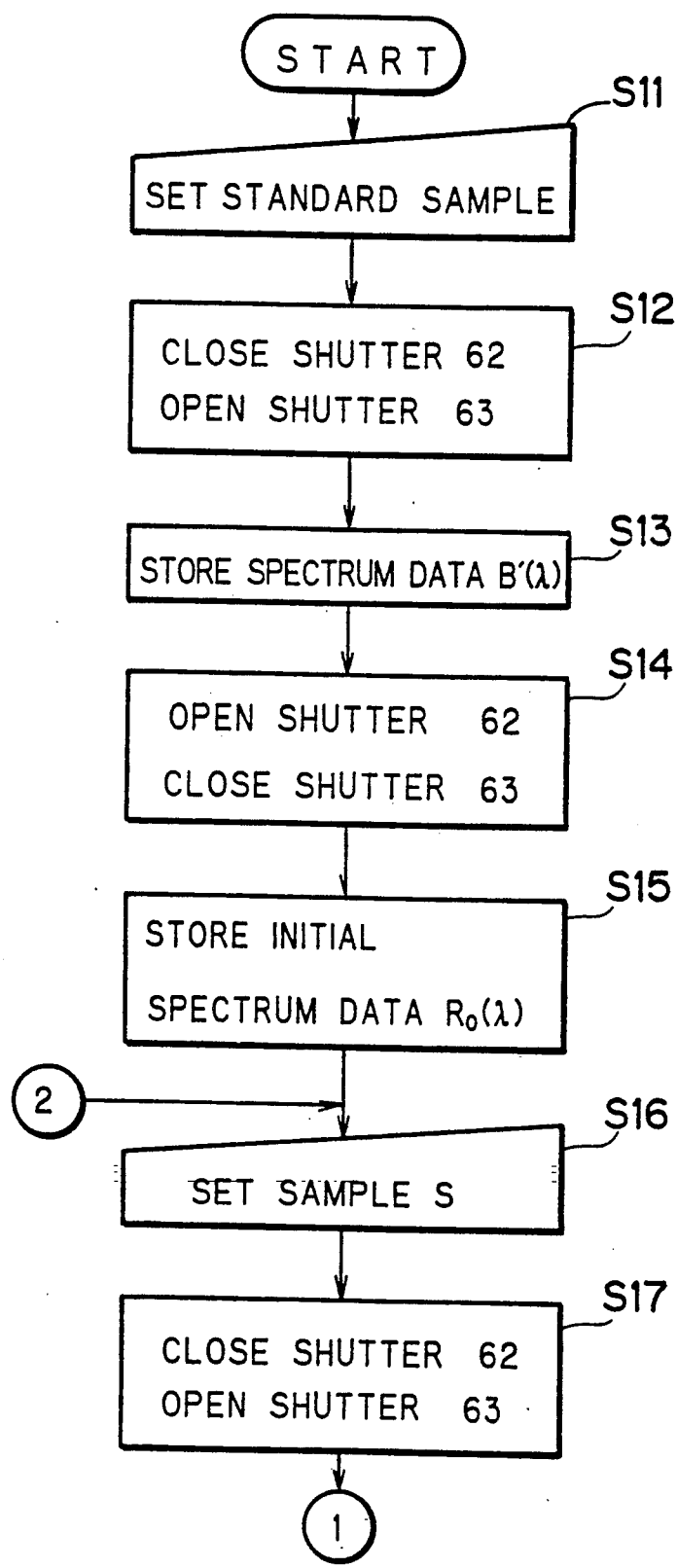

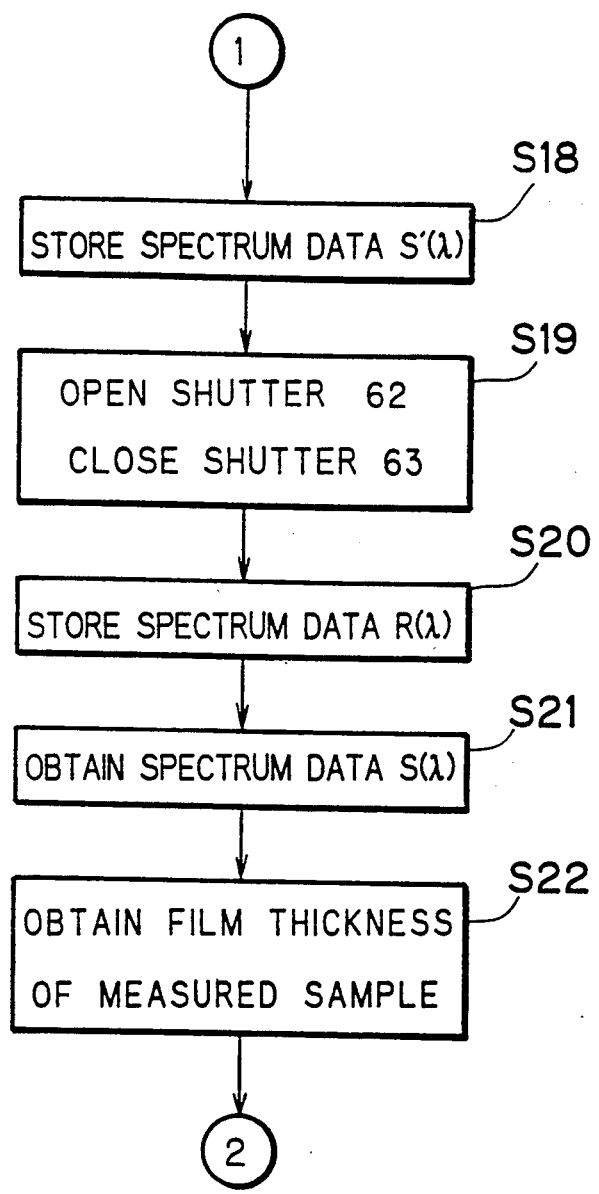

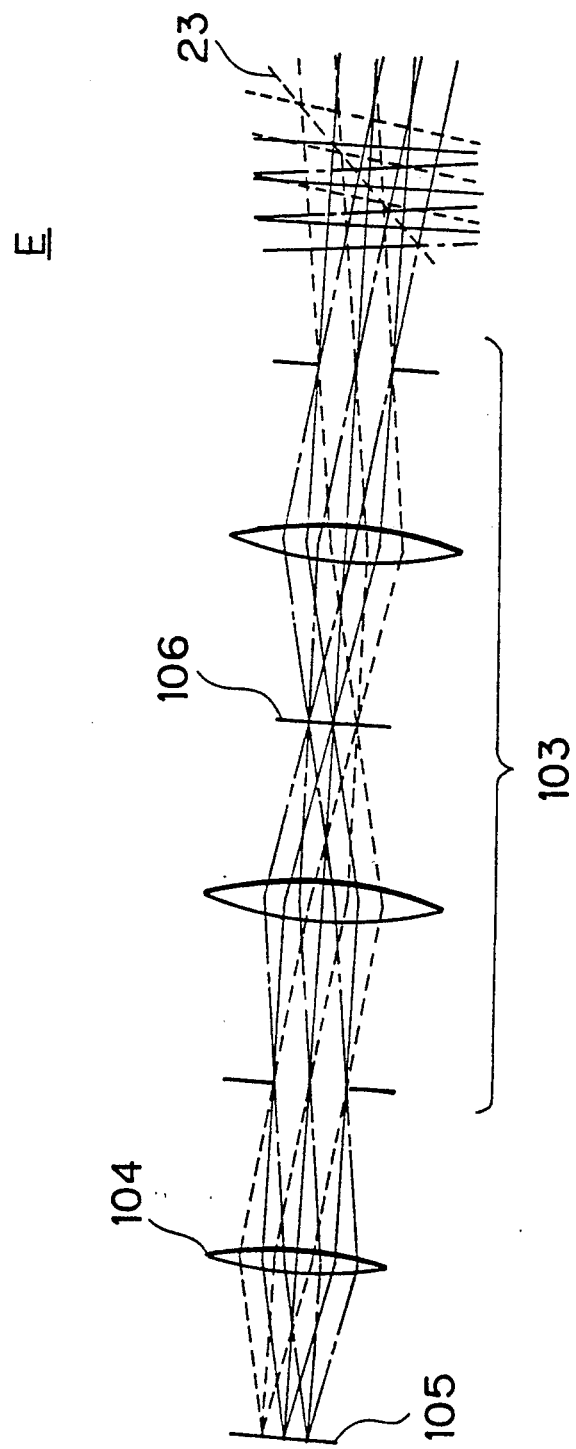

MICROSPECTROSCOPE

BACKGROUND OF THE INVENTION

1. Field of the Invention

The present invention relates to a microspectroscope for detecting the spectrum of observed light from a sample to be measured.

2. Description of the Prior Art

FIG. 1 is a schematic block diagram showing a conventional microspectroscope 1. As shown in FIG. 1, the microspectroscope 1 comprises an illuminating optical system 10, a microscopic optical system 20, a reflecting mirror 30, a spectroscopic unit 40, and a monitoring optical system 50.

The illuminating optical system 10 is formed by a light source 11, a condenser lens 12, an aperture stop 13, a field stop 14 and another condenser lens 15, so that illuminating light from the light source is guided to the microscopic optical system 20 through the condenser lens 12, the aperture stop 13, the field stop 14 and the condenser lens 15.

The microscopic optical system 20 is formed by an objective lens 21, an image-formation lens 24 and a beam splitter 23 provided between the objective lens 21 and the image-formation lens 24. Symbol 22 denotes a pupil position of the objective lens 21.

The illuminating light from the light source 11 passes through the condenser lens 12, the aperture stop 13, the field stop 14 and the condenser lens 15, and is guided to the objective lens 21 by the beam splitter 23. The illuminating light transmitted through the objective lens 21 is applied onto the surface of a sample S which is supported by a sample holder (not shown).

Reflected light reflected by the surface of the sample S is directed through the objective lens 21, the beam splitter 23 and the image-formation lens 24 to be enlarged and imaged at a location close to the reflecting mirror 30.

The reflecting mirror 30 is provided with a pinhole 31. Within the reflected light, therefore, reflected light $L_S$ (which passes through the pinhole 31) is received by the spectroscopic unit 40.

The spectroscopic unit 40 is formed by a diffraction grating 41 for separating the reflected light $L_S$ into spectral components and a photo detector 42 for detecting the spectrum of the light spectrally diffracted by the diffraction grating 41. The diffraction grating 41 may be a flat field type diffraction grating which images a spectrum on a flat plane, for example. Alternatively, the diffraction grating 41 may have a sweeper. The photo detector 42, which is formed by a photodiode array or a CCD, for example, is conjugate with the pinhole 31. Alternatively, the photo detector 42 may be a photomultiplier.

The reflected light $L_S$ received by the spectroscopic unit 40 is separated into its spectral components by the diffraction grating 41, and the respective spectral components of the light $L_S$ are received by the photo detector 42, which in turn outputs a signal corresponding to the spectrum of the light $L_S$.

The reflected light that is reflected by the reflecting mirror 30 enters the monitoring optical system 50, and is imaged on an image-formation position 52 through a relay lens 51. Thus, an enlarged image of the surface of the sample S is imaged on an image-formation plane, so that the measuring position of the sample S can be confirmed and focusing can be performed on the basis of the enlarged image.

When illuminating light is applied onto the surface of a sample S which comprises a substrate and a transparent thin film formed thereon, such as a silicon substrate and a silicon oxide film, for example, light reflected by the surface of the thin film and light transmitted through the thin film and then reflected by the surface of the substrate interfers with each other within the microspectroscope. The degree of such interference depends on the indexes of refraction of the substrate and the thin film, the thickness of the thin film and the wavelength of the illuminating light.

Since the indexes of refraction of the substrate and the thin film and the wavelength of the illuminating light are constant the degree of interference of the reflected light depends solely on the thickness of the thin film. The microspectroscope 1 outputs a detection signal relating to the spectrum which is responsive to the thickness of the thin film. Therefore, the conventional microspectroscope 1 is generally useful within to a film thickness measuring apparatus.

As shown in FIG. 1, such a film thickness measuring apparatus 2 is formed by the microspectroscope 1 and an arithmetic unit 3, so that the microspectroscope 1 detects the spectrum of the sample S and the arithmetic unit 3 computes the film thickness of the sample S on the basis of spectral data obtained by the microspectroscope 1.

The spectrum detected by the microspectroscope 1 is influenced by various factors such as spectral transmittance characteristics of the illuminating optical system 10 and and the microscopic optical system 20, luminous energy loss caused when the light passes through these optical systems, the spectral characteristic of the diffraction grating 41, the spectral-response characteristic of the photo detector 42, and the like. In order to accurately measure the film thickness of the sample S, it is necessary to eliminate such influences.

Thus, errors caused by such factors are calibrated as follows:

FIG. 2 is a flow chart showing a method of measuring film thickness by the film thickness measuring apparatus 2. Prior to measurement, an operator inputs spectrum data $B(\lambda)$ of a sample (hereinafter referred to as "standard sample") in the arithmetic unit 3 through a keyboard (not shown). The spectrum data of the standard sample is known in the data. The known is stored in a memory (not shown) provided in the arithmetic unit 3. The standard sample may be a silicon substrate, a substrate which is deposited with aluminum on its surface, or the like.

Then the operator sets the standard sample on the sample holder of the microspectroscope (step S1), and supplies a command signal for detecting calibration data to the arithmetic unit 3. In response to a command from the arithmetic unit 3, the microspectroscope detects the spectrum of the standard sample and stores data $B'(\lambda)$ relating to the spectrum in the memory of the arithmetic unit 3 (step S2).

Then, the operator removes the standard sample from the sample holder of the microspectroscope 1 and sets the sample S on the sample holder of the microspectroscope 1 (step S3). Thereafter the operator supplies a command to the arithmetic unit 3 for starting measurement, so that the microspectroscope 1 detects the spectrum of the sample S in response to a command outputted from the arithmetic unit 3, and data $S'(\lambda)$ relating to the spectrum of the sample S is stored in the memory of the arithmetic unit 3 (step S4).

At a step S5, the data S'(λ), B(λ) and B'(λ) stored in the memory are read in the arithmetic unit 3, to obtain data S(λ) in accordance with the following expression:

$$S(\lambda) = \frac{B(\lambda)}{B'(\lambda)} \cdot S'(\lambda) \qquad (1)$$

The data S(λ) corresponds to a signal outputted from the microspectroscope 1 on the assumption that absolutely no influence is caused by the aforementioned factors. In other words, the data S(λ) shows the true spectrum of the sample S.

Using the data S(λ) the arithmetic unit 3 comprises the thickness of the thin film (step S6). This computation is itself well known and hence description thereof is omitted.

As understood from the expression (1), the data S'(λ) relating to the actually measured spectrum is calibrated to obtain the data S(λ) relating to the true spectrum, whereby the film thickness can be accurately measured.

Further, since the aforementioned factors are not influenced by peripheral environmental changes around the apparatus 2 such as temperature, humidity etc. but remain constant, the data B'(λ) once measured will not be significantly changed. Therefore, the steps S3 to S6 are continuously repeated to measure the thickness of a subsequent sample S. to thereby continuously accurately measure the film thickness.

However, the spectrum also influenced by factors other than the above, such, as, spectral emissivity which is change with ambient temperature of the light source 11, for example. When the ambient temperature of the light source 11 changes, spectral emissivity changes accordingly, to vary the spectrum actually measured by the microspectroscope 1. It is assumed here that the light source 11 has a certain spectral emissivity characteristic (hereinafter referred to as "first characteristic") in measurement of the data B'(λ) at the step S2, for example When the characteristic of the light source 11 affecting detection of the spectrum of the sample S is substantially identical to the first characteristic, the film thickness can be measured with no particular problem.

However, when a plurality of samples S are continuously measured and the light source 11 has a second characteristic which differs significantly from the first characteristic after a certain period of time, measurement accuracy is reduced. This is because the data S'(λ) is detected by illuminating light from the light source 11 which has the second characteristic, although the data B'(λ) is detected by the illuminating light from the light source 11 which has the first characteristic.

To continuously maintain correct measurement, therefore, it is necessary to frequently measure the data B'(λ) after measuring the film thickness of the sample S, as shown by dotted lines in FIG. 2. In this case, efficiency is reduced since the standard sample must be replaced on the sample holder of the microspectroscope 1.

SUMMARY OF THE INVENTION

The present invention relates to a method of and an apparatus for obtaining spectral data and calculating corrected spectral data. The method includes the steps of: obtaining spectral data S'(λ) which is representative of the spectral characteristics of light which is generated by a light source and reflected by an object; substantially concurrently with the step of obtaining the spectral data S'(λ), obtaining spectral data R(λ) which is representative of the spectral characteristics of light which is generated by the light source; and calculating corrected spectral data S(λ) as a function of the spectral data S'(λ) and the spectral data R(λ).

The present invention also relates to an optical system, including: (A) a light source, (B) a sample holder; (C) reflecting means; (D) a spectroscopic unit; and (E) a beam splitter for: (1) transmitting light from the light source toward the sample holder and transmitting light reflected from the sample holder toward the spectroscopic unit so as to obtain spectral data which is representative of light reflected from the sample holder; and (2) transmitting light from the light source toward the reflecting means and transmitting light reflected by the reflecting means toward the spectroscopic unit so as to obtain spectral data which is representative of light from the light source.

The present invention also relates to an optical system, including: (A) a light source; (B) a sample holder; (C) a first spectroscopic unit and a second spectroscopic unit; and (D) a beam splitter for: (1) transmitting light from the light source toward the sample holder toward the first spectroscopic unit so as to obtain spectral data which is representative of light reflected from the sample holder; and (2) transmitting light from the light source toward the second spectroscopic unit so as to obtain spectral data which is representative of light from the light source.

The present invention also relates to an optical system, including: a light source; a sample holder; a spectroscopic unit; means for transmitting light from the light source toward the sample holder and for transmitting light reflected from the sample holder toward the spectroscopic unit so as to obtain spectral data which is representative of the spectral characteristics of light which is reflected from the sample holder; and intercepting means for transmitting light from the light source toward the spectroscopic unit so as to obtain spectral data which is representative of the spectral characteristics of light from the light source, the intercepting means being located within the light source and the sample holder.

An object of the invention is to provide a microspectroscope which can more easily prevent reduction in detection accuracy caused by variations in ambient temperature, humidity and the like.

Another object of the present invention is to provide a microspectroscope which is simple in detection procedure.

These and other objects, features, aspects and advantages of the present invention will become more apparent from the following detailed description of the preferred embodiments when taken in conjunction with the accompanying drawings.

BRIEF DESCRIPTION OF THE DRAWINGS

FIG. 3 is a schematic block diagram showing a microspectroscope according to a first embodiment of the invention;

FIG. 4 is a flow chart showing a method of measuring film thickness using the microspectroscope shown in FIG. 3;

FIG. 9B illustrates an essential part of the microspectroscope of the fifth embodiment;

DESCRIPTION OF THE PREFERRED EMBODIMENTS

A. First Embodiment

Figure 1:
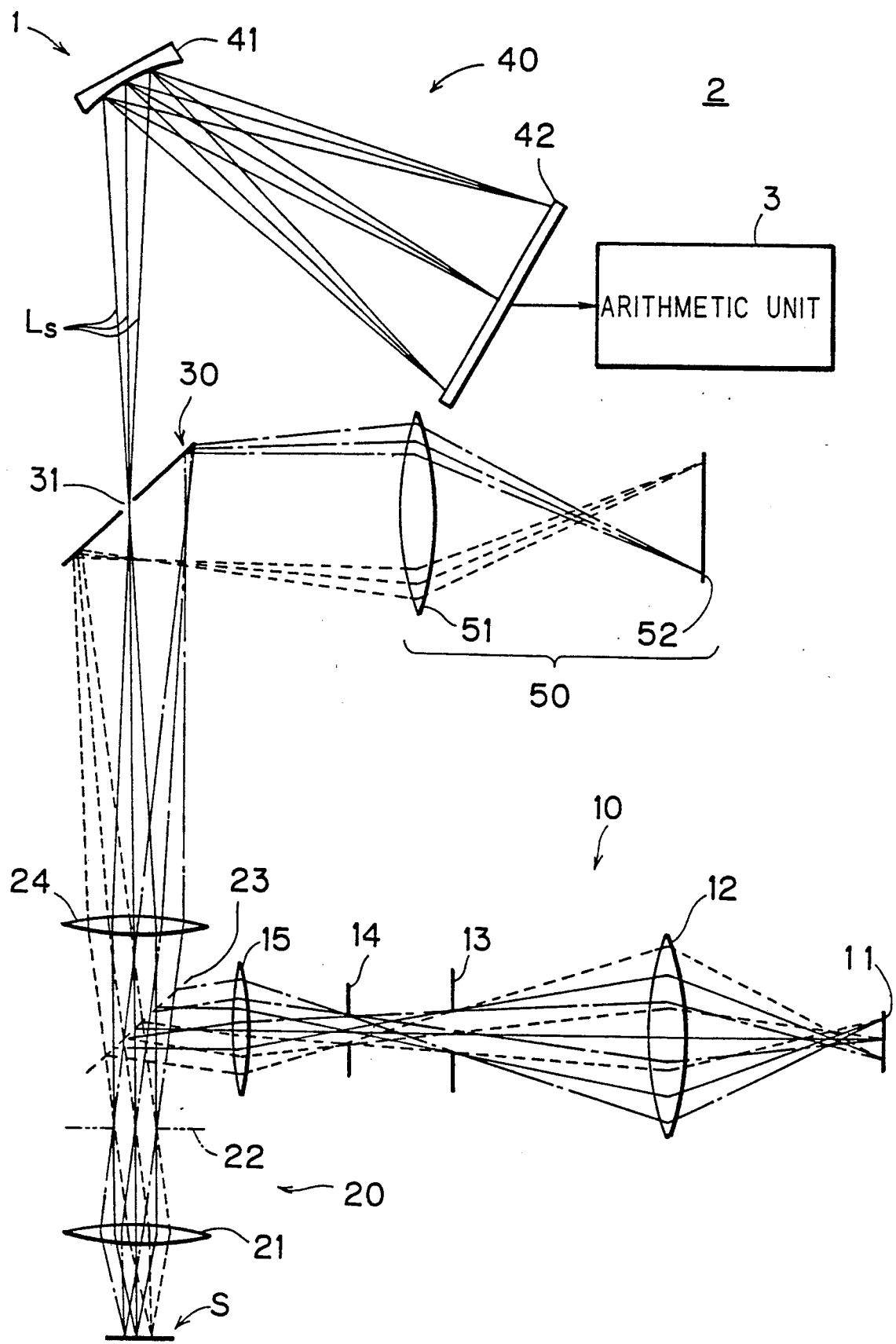
FIG. 1 is a schematic block diagram showing a conventional microspectroscope.
Figure 2:
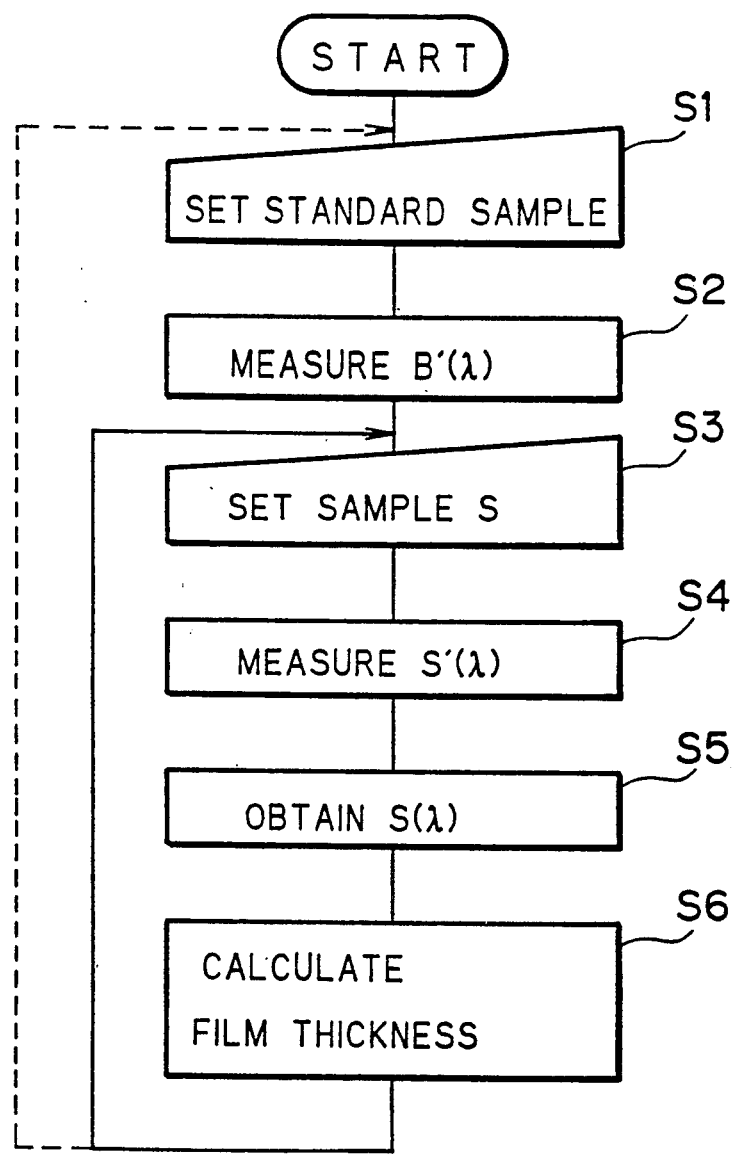
FIG. 2 is a flow chart showing a method of measuring film thickness using the microspectroscope shown in FIG. 1.

Referring to FIG. 3 a microspectroscope A is formed by an illuminating optical system 10, a microscopic optical system 20, a reflecting mirror 30, a spectroscopic unit 40, a monitoring optical system 50, anther reflecting mirror 61, and shutters 62 and 63. The illuminating optical system 10, the microscopic optical system 20, the reflecting mirror 30, the spectroscopic unit 40, and the monitoring optical system 50 are identical to those in the prior art shown in FIG. 1, and hence redundant description is omitted.

The reflecting mirror 61 is provided on an optical path of illuminating light from a light source 11 symmetrical with a pupil position 22 with respect to a beam splitter 23. The position of the reflecting mirror 61 is not restricted to this but may be slightly moved on the optical path of the illuminating light. The reflecting mirror 61 desirably has substantially uniform spectral reflectance within a wavelength range, and is formed of a mirror deposited with aluminum, etc.

The shutter 62 is located between the reflecting mirror 61 and the beam splitter 23, while the other shutter 63 is located between the pupil position 22 of an objective lens 21 and the beam splitter 23. The shutters 62 and 63 are opened and closed by commands from an arithmetic unit 4. The shutter 63 need not be between the pupil position 22 and the beam splitter 23, but may be appropriately located between a sample S and the beam splitter 23.

The microspectroscope A can be used in a film thickness measuring apparatus, similarly to the prior art. Symbol AA in FIG. 3 denotes a film thickness measuring apparatus. The film thickness measuring apparatus AA is formed by the microspectroscope A and the arithmetic unit 4. The unit 4 operates film thickness in accordance with the following computes film thickness while controlling the microspectroscope A as follows:. thickness measuring apparatus AA, an operator inputs data $B(\lambda)$ relating to a known spectrum of a standard sample in the arithmetic unit 4 through a keyboard (not shown) to store the same in a memory (not shown) within in the arithmetic unit 4. The operator further previously computes data ("reference data") relating to the spectrum with respect to thickness of a thin film on the basis of indexes of reflection of a substrate and the thin film of the sample S every constant thickness space and inputs the result of this computation in the arithmetic unit 4 through the keyboard, to store the result in the memory.

Then the operator sets the standard sample in a sample holder (step S11) and supplies a command to the arithmetic unit 4 for detecting calibration data. In response to commands from the arithmetic unit 4, the shutters 62 and 63 are closed and opened, respectively, (step S12) so that illuminating light from the light source 11 is applied to the surface of the standard sample when the light source 11 is turned on. Observed light reflected by the surface of the standard sample is enlarged and imaged close to the reflecting mirror 30. Observed light $L_S$ passes through a pinhole 31 and is received by the spectroscopic unit 40. The unit 40 in turn detects the spectrum of the observed light $L_S$. Further, data $B'(\lambda)$ relating to the spectrum is supplied from a photo detector 42 to the arithmetic unit 4, and stored in the memory (step S13).

Immediately after the step S13, the shutters 62 and 63 are opened and closed state, respectively, in response to commands from the arithmetic unit 4 (step S14). The light source 11 is turned on and illuminating light is applied to the reflecting mirror 61 through the beam splitter 23 and the shutter 62. Reflected light reflected by the mirror 61 is guided toward the image-formation lens 24 by the beam splitter 23, to be enlarged and imaged close to the reflecting mirror 30. Reflected light $L_R$ passes through the pinhole 31 and is received by the spectroscopic unit 40 such that the photo detector 42 detects the spectrum of the reflected light $L_R$. Data $R_0(\lambda)$ relating to the spectrum is supplied from the photo detector 42 to the arithmetic unit 4, to be stored in the memory (step S15). The data $R_0(\lambda)$ is representative of the spectral emmissivity of the light source 11.

The operator them removes the standard sample from the sample holder and sets the sample S in the sample holder (step S16). Then, the operator supplies a command to the arithmetic unit 4 to start measurement. The microspectroscope A is thus controlled in response to a command outputted from the arithmetic unit 4, to correctly measure the film thickness of the sample S as follows:

The shutters 62 and 63 are closed and opened, respectively, (step S17) so that the spectrum of observed light $L_S$ is detected, and data $S'(\lambda)$ relating to the spectrum of the observed light $L_2$ is stored in the memory of the arithmetic unit 4 (step S18).

Immediately after the step S18, the shutters 62 and 63 are opened and closed, respectively, (step S19), so that the spectrum of the reflected light $L_R$ is detected and data $R(\lambda)$ relating to the spectrum of the reflected light $L_R$ is stored in the memory of the arithmetic unit 4 (step S20).

Thereafter the data $B(\lambda)$, $B'(\lambda)$, $S'(\lambda)$, $R(\lambda)$ and $R_0(\lambda)$ formed in the memory are read, so that data $S(\lambda)$ is obtained in accordance with the following expression (step S21):

$$S(\lambda) = \frac{R_0(\lambda) \cdot B(\lambda)}{R(\lambda) \cdot B'(\lambda)} \cdot S'(\lambda) \quad (2)$$

Even if the light source 11 has a second characteristic in measurement of the data S'(λ) (step S18) while the same has a first characteristic in measurement of the data B'(λ) (step S13), the data S(λ) relating to the spectrum of the sample S can be correctly detected since the amount of variation in spectral emissivitY of the light source 11 is corrected on the basis of the data R₀(λ) and R(λ).

Thereafter, the data S(λ) is compared with reference data stored in the memory, to obtain the film thickness of the sample S (step S22).

As understood from the expressiOn (2), the data S'(λ) (relating to the actually measured spectrum) is calibrated, whereby the film thickness can be accurately measured.

After the operator replaces the sample S, the aforementioned steps S17 to S22 are repeated so as to continuously measure film thickness. the sample S.

Errors caused by variation in spectral emissivity of the light source 11 can be corrected by simply opening and closing the shutters 62 and 63. As a result, efficiency is improved.

The data R(λ) can be detected either immediately after detection of the data S'(λ), or immediately before detection of the data S'(λ).

Further, the method of obtaining film thickness on the basis of the data S(λ) is not restricted to the above but a well-known method such as that disclosed in Japanese Patent Laying-Open Gazette No. 217705/1986 is also applicable.

B. Second Embodiment

Figure 5:
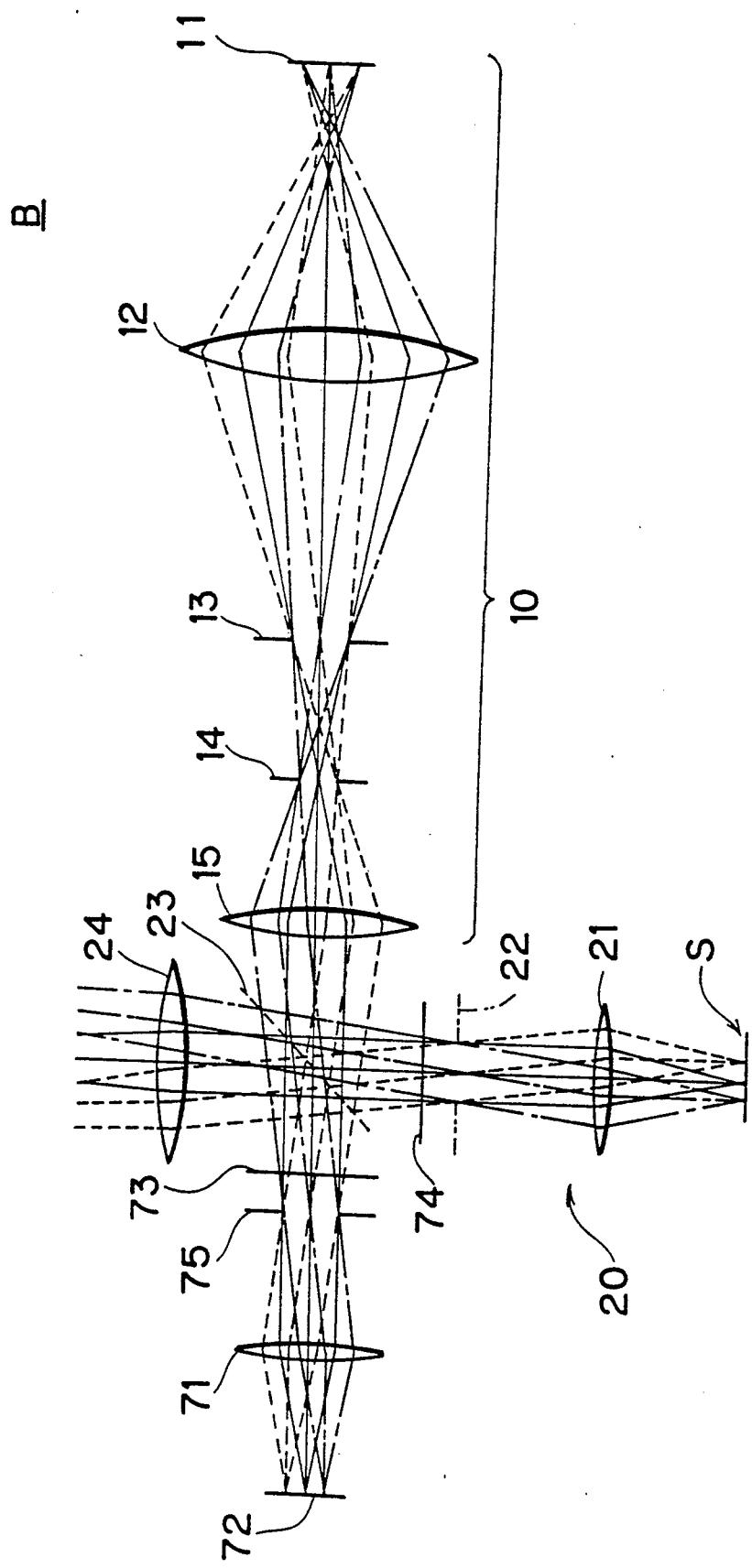
FIG. 5 illustrates a microspectroscope according to second embodiment of the invention.

FIG. 5 is a block diagram showing an essential part of a microspectroscope according to a second embodiment of the present invention. An illuminating optical system 10, a microscopic optical system 20, an objective lens 71, a reflecting mirror 72 and shutters 73 and 74, which are components of a microspectroscope B, are shown in FIG. 5. Other components (reflecting mirror 30, spectroscopic unit 40 and mOnitoring optical system 50) are identical to those of the first embodiment, and not shown in the figure. Numeral 75 denotes a pupil position of the objective lens 71.

The objective lens 71, which is substantially identical in spectral transmittance and aperture number to an objective lens 21, is located symmetrically to the objective lens 21 of the microscopic optical system 20 with respect to a beam splitter 23. The reflecting mirror 72 is provided in a front focal position of the objective lens 71. The shutters 73 and 74 are arranged between the beam splitter 23 and the pupil positions 75 and 22, respectively.

Since the second embodiment is substantially identical in structure to the first embodiment (as understood from a comparison of FIGS. 3 and 5) the microspectroscope B can be applied to a film thickness measuring apparatus. Such a film thickness measuring apparatus is identical in structure to the film thickness measuring apparatus AA shown in FIG. 3 except for the objective lens 71. Operation of the apparatus of FIG. 5 is also substantially identical to that of the apparatus AA (FIG. 4). According to the second embodiment, therefore, an effect identical to that of the first embodiment can be attained.

Figure 6:
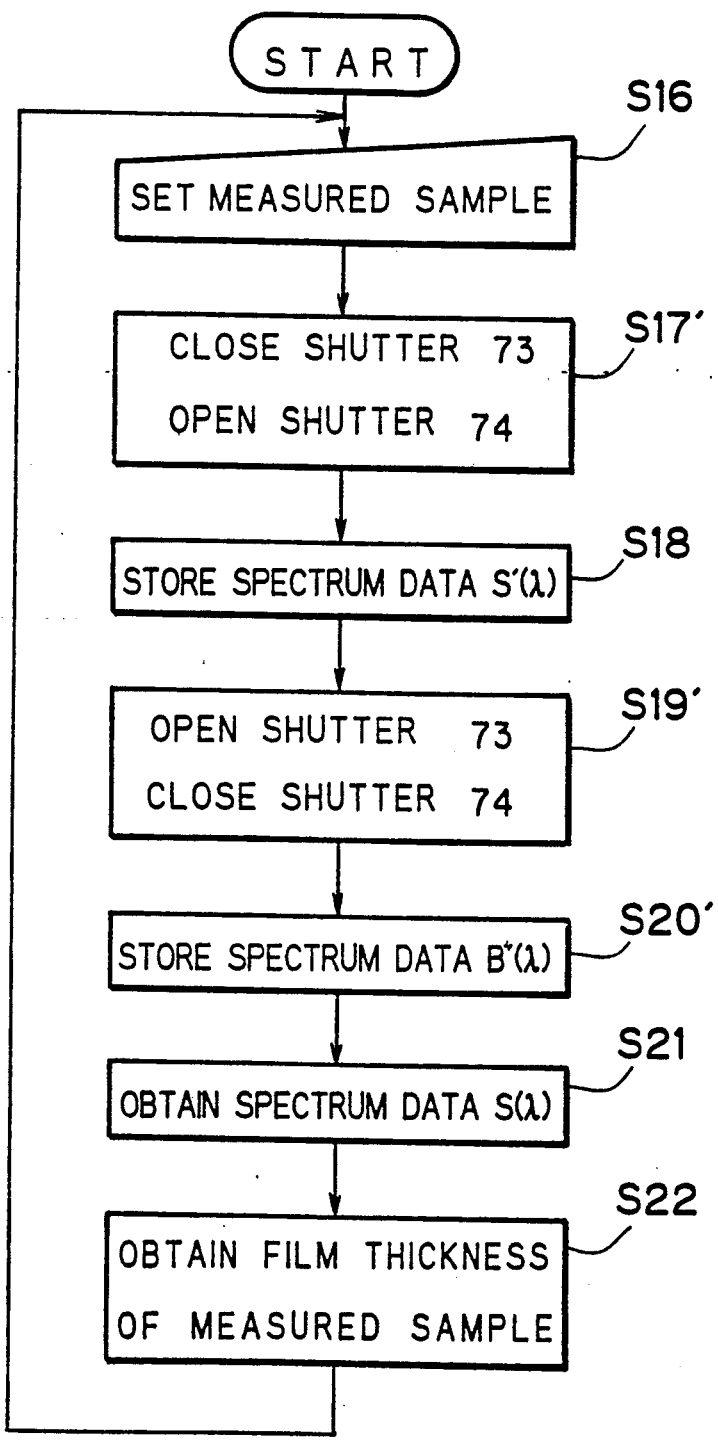
FIG. 6 is a flow chart of a method of measuring film thickness using the microspectroscope shown in FIG. 5.

On the other hand, in the apparatus of FIG. 5, optical conditions between the reflecting mirror 72 and the beam splitter 23 are substantially identical to optical conditions between a sample S and the beam splitter 23. Hence, the following effect can be additionally attained when the reflecting mirror 72 is formed by a standard sample:

FIG. 6 is a flow chart showing the operation of a film thickness measuring apparatus, in which the reflecting mirror 72 is formed by a standard sample. Similarly to the first embodiment, the operator stores data B(λ) (relating to the spectrum of the standard sample) and predetermined reference data in the memory in advance of film thickness measurement.

Then the operator sets the sample S in a sample holder (step S16) and thereafter supplies a command to an arithmetic unit 4 to start measurement. The entire apparatus is controlled in response to a command from the arithmetic unit 4 so as to correctly obtain the film thickness of the sample S in the following manner:

The shutters 73 and 74 are set in a closed state and an opened state, respectively (step S17'), so that the spectrum of observed light is detected similarly to the above and data S'(λ) relating to the spectrum of the observed light is stored in the memory (step S18).

Immediately after step S18, the shutters 73 and 74 are set in an opened state and a closed state, respectively (step S19') and the spectrum of reflected light reflected by the reflecting mirror (the standard sample) 72 is detected similarly to the above, so that data B''(λ) relating to the spectrum of the reflected light is stored in the memory (step S20').

Thereafter the data B(λ), B''(λ) and S'(λ) stored in the memory are read to obtain data S(λ) in accordance with the following expression (step S21):

$$S(\lambda) = \frac{B(\lambda)}{B''(\lambda)} \cdot S'(\lambda) \quad (3)$$

There is no need to consider an error caused by variation in spectral emissivity of a light source 11, since the data B''(λ) is detected immediately after detection of the data S'(λ).

Thereafter the data S(λ) is compared with the reference data stored in the memory to obtain the film thickness of the sample S (step S22).

Film thickness can be continuously measured by repeating the steps S16 to S22.

Measurement is extremely simplified and operational efficiency is improved when the reflecting mirror 72 is formed by a standard sample.

C. Third Embodiment

Figure 7:
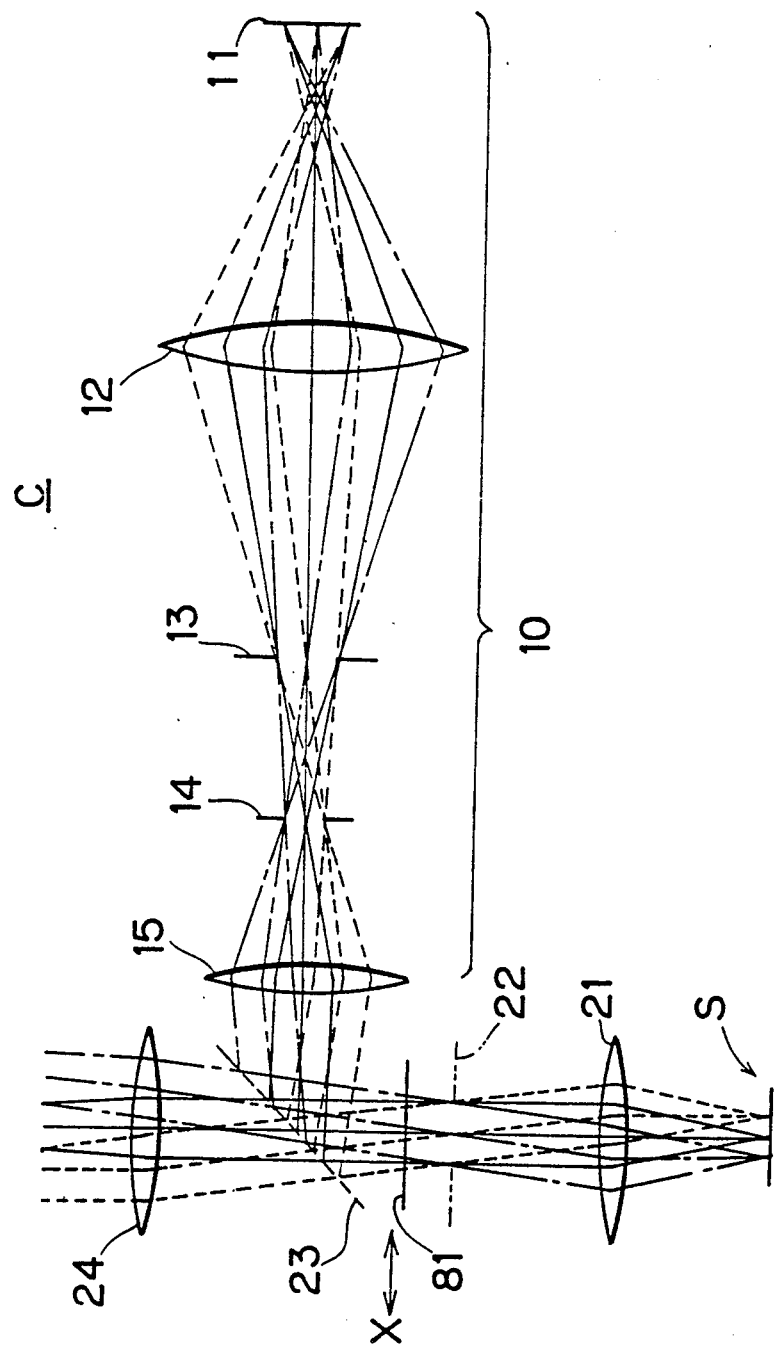
FIG. 7 illustrates an essential part of a microspectroscope according to a third embodiment of the invention.

FIG. 7 is a block diagram showing an essential part of a microspectroscope according to a third embodiment of the present invention. This microspectroscope C has a reflecting mirror 81 provided between a beam splitter 23 and a pupil position 22 in place of the reflecting mirror 61 and the shutters 62 and 63 of the first embodiment. The reflecting mirror 81 is adapted to reciprocate along an X-axis by driving means (not shown). Other structure of this embodiment is identical to that of the microspectroscope A. Thus, this microspectroscope C can be applied to a film thickness measuring apparatus.

Operation of the film thickness measuring apparatus to which the microspectroscope C is applied is identical to that of the apparatus AA except for the following two points: While the shutters 62 and 63 are set in an opened state and a closed state at the steps S14 and S19 in the film thickness measuring apparatus AA, the reflecting mirror 81 is located on an image-formation optical axis in the film thickness measuring apparatus to which the microspectroscope C is applied, as shown in FIG. 7. Further, while the shutters 62 and 63 are set in a closed state and an opened state respectively at the steps S12 and S17, the reflecting mirror 81 is move out of the image-formation optical path.

Thus, an effect similar to that of the first embodiment can be attained.

D. Fourth Embodiment

Figure 8:
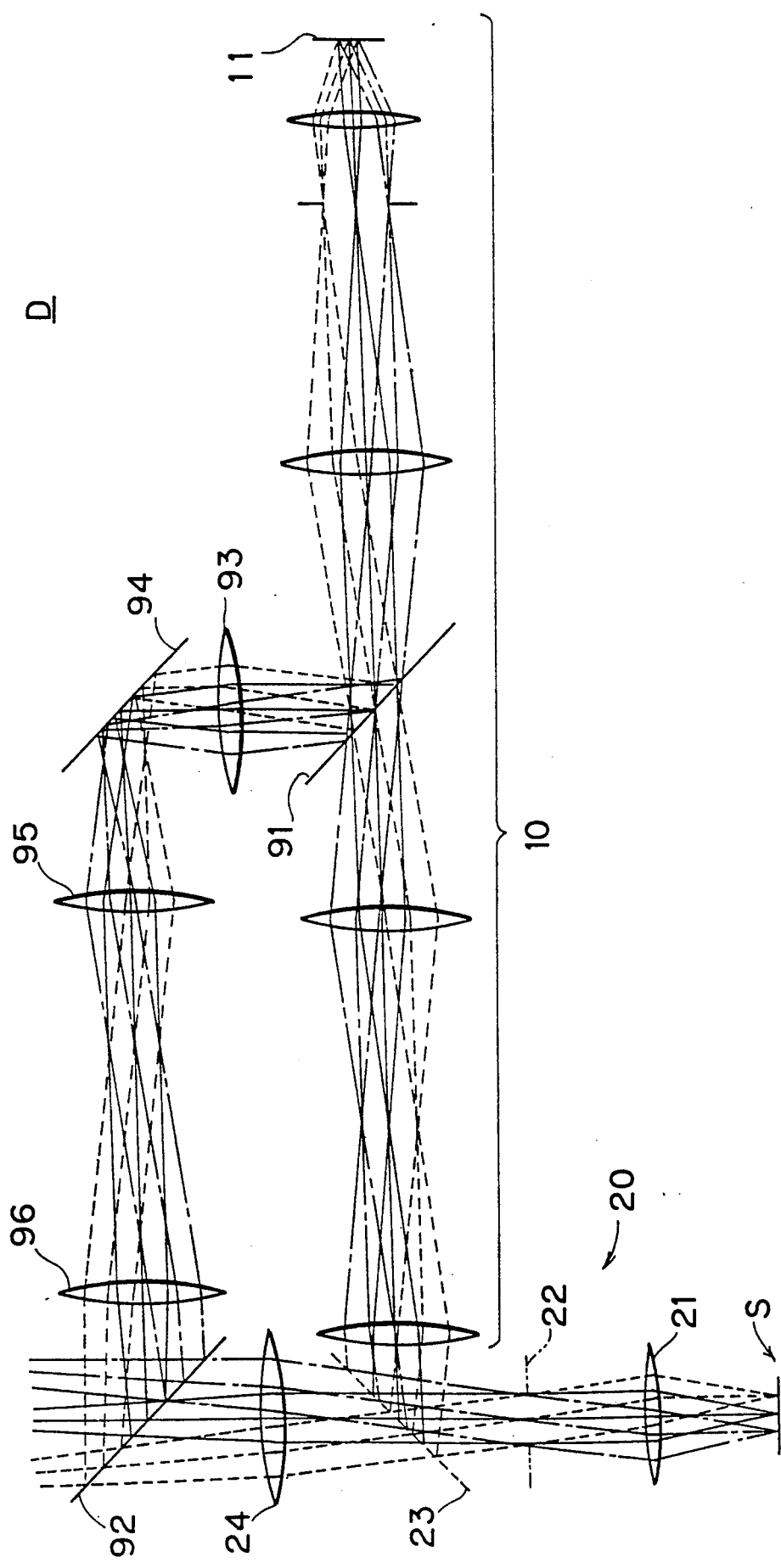
FIG. 8 illustrates an essential part of a microspectroscope according to a fourth embodiment of the invention.

FIG. 8 is a block diagram showing an essential part of a microspectroscope according to a fourth embodiment of the present invention. As shown in FIG. 8, the microspectroscope D is provided with reflecting mirrors 91, 92 and 94 and lenses 93, 95 and 96 in place of the reflecting mirror 61 and the shutters 62 and 63 of the first embodiment.

The reflecting mirrors 91 and 92 are provided in an illuminating optical system 10 and a microscopic optical system 20, respectively, and are adapted to be synchronously reciprocated in a direction perpendicular to the plane of the figure by driving means (not shown). Other structure of this embodiment is identical to that of the microspectroscope A. Thus, the microspectroscope D can be applied to a film thickness measuring apparatus.

Operation of the film thickness measuring apparatus to which the microspectroscope D is applied is identical to that of the apparatus AA, except for the following two points: While the shutters 62 and 63 are set in an opened state and a closed state respectively at the steps S14 and S19 in the film thickness measuring apparatus AA, the reflecting mirrors 91 and 92 are located on an illuminating optical path and an image-formation optical path respectively in the film thickness measuring apparatus to which the microspectroscope D is applied, as shown in FIG. 8. Accordingly, illuminating light outgoing from a light source 11 is not applied to the surface of a sample S, but guided to an image-formation position side of the microscopic optical system 20 through the reflecting mirror 91, the lens 93, the reflecting mirror 94, the lenses 95 and 96 and the reflecting mirror 92. Further, while the shutters 62 and 63 are set in a closed state and an opened state respectively at the steps S12 and S17 in the film thickness measuring apparatus AA, the reflecting mirrors 91 and 92 are moved to out of the illuminating optical path and the image-formation optical path.

Thus, an effect similar to that of the first embodiment can be attained.

E. Fifth Embodiment

Figure 9A:
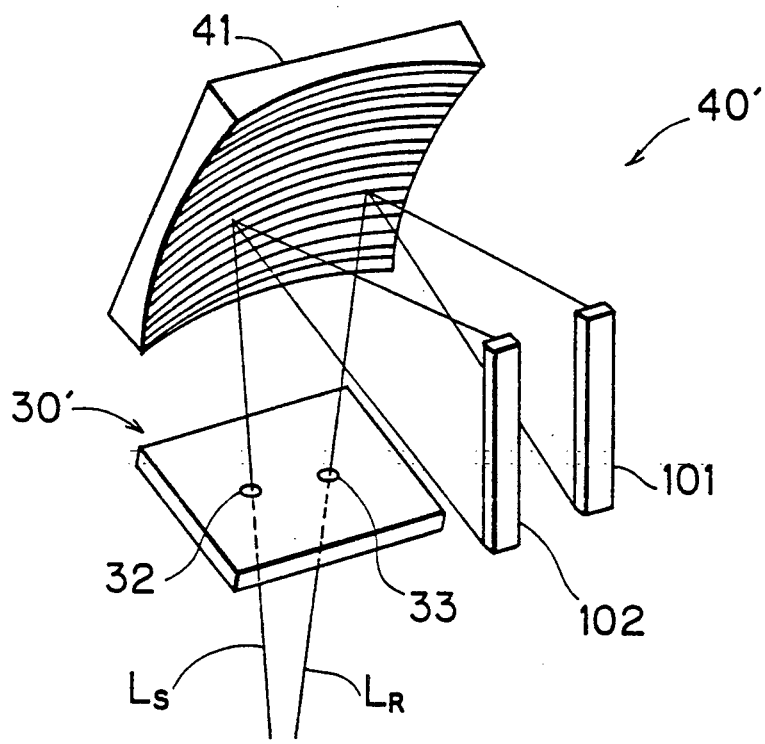
FIG. 9A is a perspective of an essential part of a microspectroscope according to a fifth embodiment of the invention.

FIG. 9A is a perspective view showing an essential part of a microspectroscope according to a fifth embodiment of the present invention. FIG. 9B is a block diagram showing another essential part of the fifth embodiment. FIG. 9A shows a reflecting mirror 30' and a spectroscopic unit 40' which are components of a microspectroscope E. FIG. 9B shows a beam splitter 23, a relay lens 103 a lens 104, a reflecting mirror 105 and a filter 106 which are also components of the microspectroscope E Other components (illuminating optical system 10, microscopic optical system 20, monitoring optical system 50 and arithmetic unit 4) are identical to those of the first to fourth embodiments, and omitted from the figures.

As shown in FIG. 9A, the reflecting mirror 30' is provided with a pinhole 32 for transmitting only observed light and a spaced apart pinhole 33 for simultaneously transmitting only reflected light. To detect spectra of the observed light passing through the pinhole 32 and the reflected light passing through the pinhole 33, photo detectors 101 and 102 are provided in conjugation with the pinholes 33 and 32, respectively.

Figure 9C:
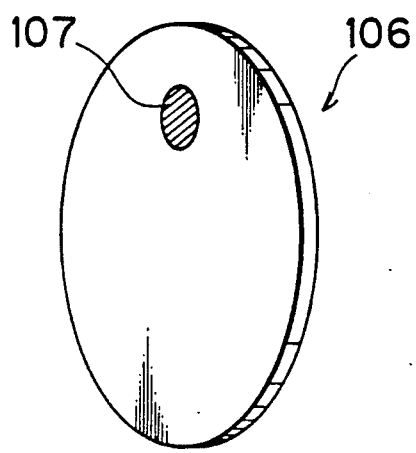
FIG. 9C is a perspective view of a component of the microspectroscope of FIGS. 9A and 9B.

As shown in FIG. 9B, the illuminating light transmitted through the beam splitter 23 is applied to the reflecting mirror 105 through the relay lens 103 and the objective lens 104. The relay lens 103 is provided with a filter 106. The filter 106 has a shielding region 107 (FIG. 9C) in a position corresponding to the pinhole 32. Within reflected light reflected by the reflecting mirror 105, therefore, light corresponding to the shielding region 107 is not applied to the pinhole 32.

Another lens (not shown) equivalent to the relay lens 103 is also provided between the beam splitter 23 and the objective lens 21. This lens is provided with a filter having a shielding region in a position corresponding to the pinhole 33. Within the observed light reflected by a sample S, therefore, light corresponding to the shielding region is not applied to the pinhole 33.

When a light source 11 is turned on, illuminating light from the light source 11 is applied to the reflecting mirror 105 through the beam splitter 23, the relay lens 103 and the objective lens 104. Reflected light reflected by the reflecting mirror 105 is guided toward an image-formation lens 24 by the beam splitter 23, to be enlarged and imaged in a position close to the reflecting mirror 30' through the image-formation lens 24. However, because of the shielding region 107, the reflected light is not applied to the pinhole 32.

Similarly, the illuminating light is also applied to the surface of the sample S, so that the observed light reflected by the surface of the sample S is enlarged and imaged in a position close to the reflecting mirror 30' through the beam splitter 23 and the image-formation lens 24. However, because of the shielding region of the filter the observed light is not applied to the pinhole 33.

Only reflected light $L_R$ passes through the pinhole 33. As a result the photo detector 101 only detects the spectrum of the reflected light $L_R$. Only observed light $L_S$ passes through the pinhole 32. Therefore, the photo detector 102 only detects the spectrum or the observed light $L_S$.

With the embodiment of FIG. 9, the spectra of the reflected light $L_R$ and the observed light $L_S$ can be simultaneously detected. This simplifies the detection procedure as compared with the first to fourth embodiments.

In this embodiment, data $R(\lambda)$ relating to the spectrum of the reflected light $L_R$ and data $S'(\lambda)$ relating to the spectrum of the observed light $L_S$ need not be stored in a memory. Since the data $R(\lambda)$ and $S'(\lambda)$ are simultaneously detected, the true data $S'(\lambda)$ can be obtained without having to store the data $S'(\lambda)$ and $R(\lambda)$. When the data $R(\lambda)$ and $S'(\lambda)$ ere detected, the ratio of the data $S'(\lambda)$ to $R(\lambda)$ is obtained (through hardware having an appropriate arithmetic circuit). Thereafter, the arithmetic unit 4 reads data $R_0(\lambda)$ (stored in the memory) and then multiplies the same by the ratio to obtain the data $S(\lambda)$.

F. Sixth Embodiment

Figure 10:
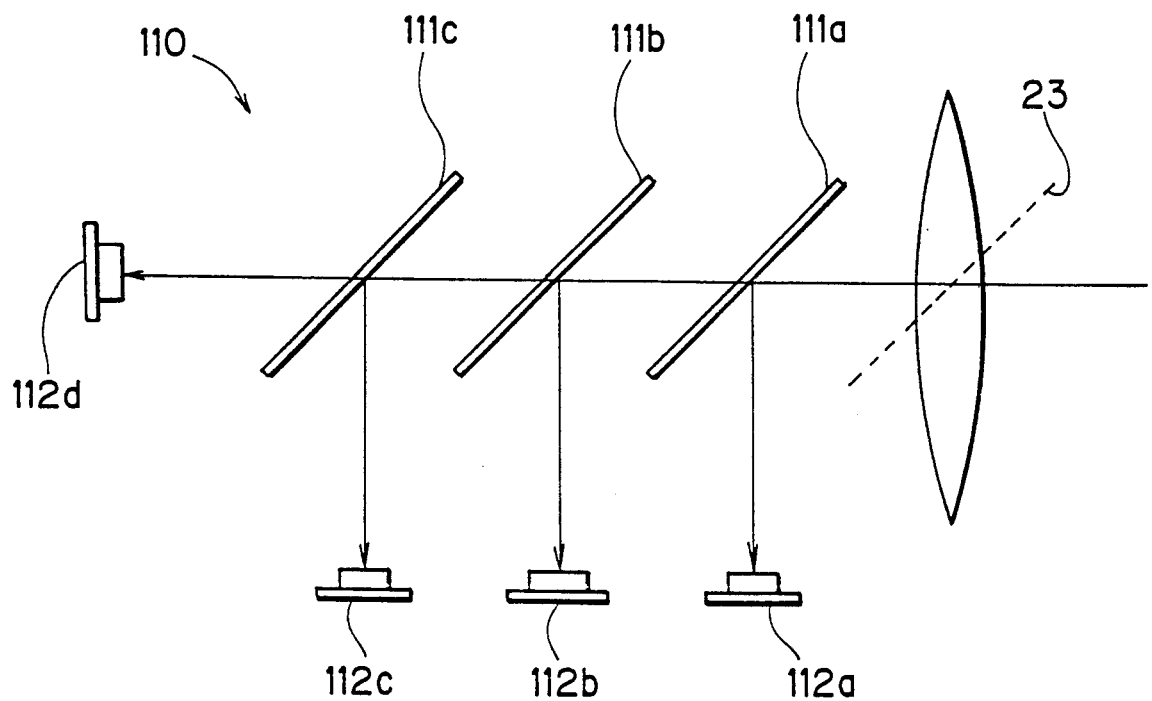
FIG. 10 illustrates an essential part of a microspectroscope according to a sixth embodiment of the invention.

FIG. 10 is a block diagram showing an essential part of microspectroscope according to a sixth embodiment of the present invention. As shown in FIG. 10, this microspectroscope F is provided with a spectroscopic unit 110 on an illuminating optical path. Other components (illuminating optical system 10 microscopic optical system 20, reflecting mirror 30, spectroscopic unit 40 and monitoring optical system 50) are identical to those of the aforementioned embodiments, and omitted from the figure.

As shown in FIG. 10, the spectroscopic unit 110 is formed by optical filters 111a, 111b and 111c provided on the optical path of illuminating light for reflecting only light components of prescribed wavelengths and photo detectors 112a, 112b, 112c and 112d such as photodiodes provided in correspondence to the optical filters 111a, 111b and 111c, respectively. The number of the optical filters 111a, 111b and 111c is not restricted to three. The number depends on the characteristics of a light source 11, accuracy of measurement etc.

When the light source 11 is turned on, the illuminating light from the light source 11 is transmitted into the spectroscopic unit 110 and the spectrum of the illuminating light is detected by the photo detectors 112a, 112b and 112c. Simultaneously observed light $L_S$ is transmitted into the spectroscopic unit 40 and the spectrum of the observed light $L_S$ is detected by a photo detector 42 as in the prior art.

Thus, an effect similar to that of the fifth embodiment can be attained.

G. Seventh Embodiment

Figure 11:
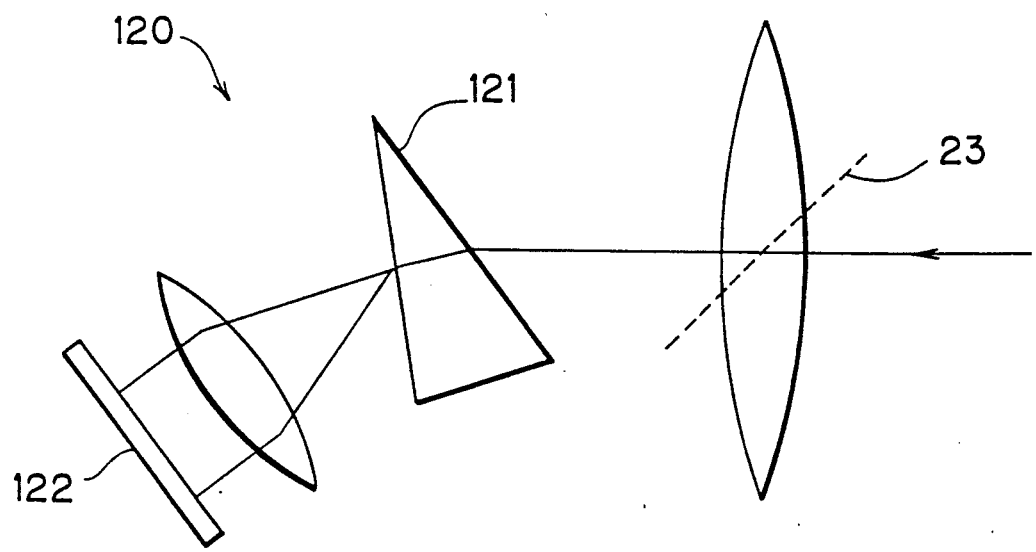
FIG. 11 illustrates an essential part of a microspectroscope according to a seventh embodiment of the invention.

FIG. 11 is a block diagram showing an essential part of a microspectroscope according to a seventh embodiment of the present invention. As in the sixth embodiment, this microspectroscope G is provided with a spectroscopic unit 120 on an illuminating optical path.

As shown in FIG. 11, the spectroscopic unit 120 is formed by a prism 121 provided on the optical path of illuminating light and a photo detector 122 (such as a CCD) for detecting the spectrum obtained through the prism 121.

When a light source 11 is turned on, illuminating light from the light source 11 is transmitted into spectroscopic unit 120 and the spectrum of the illuminating light is detected as in the sixth embodiment. Simultaneously observed light $L_S$ is transmitted into a spectroscopic unit 40 and the spectrum of the observed light $L_S$ is detected by a photo detector 42 as in the prior art.

Thus, an effect similar to that of the fifth and sixth embodiments can be attained.

H. Other Embodiments

Figure 12:
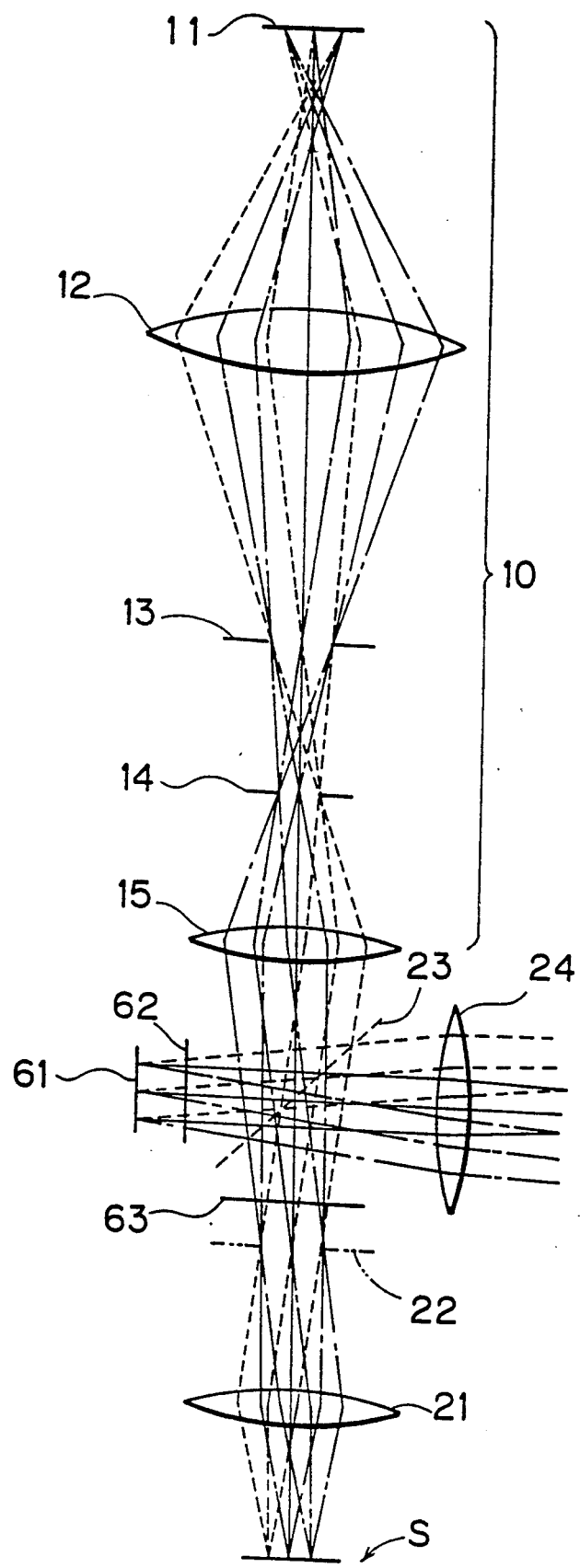
FIG. 12 illustrates an essential part of a microspectroscope according to an eighth embodiment of the present invention.

The present invention is not restricted to the aforementioned embodiments. The first embodiment (FIG. 3) may be modified to include structure formed by the illuminating optical system 10 of the first embodiment and other structure formed by a microscopic optical system 20, a reflecting mirror 30, a spectroscopic unit 40 and a monitoring optical system 50 each other, as shown in FIG. 12, for example.

Further, the diffraction grating 41 is of the first to fifth embodiments may be replaced by another optical element having a spectroscopic function, such as a prism.

Although the above embodiments have been described with reference to the so-called reflection type microspectroscopes, the fourth, sixth and seventy embodiments may also be applied to the so-called transmission type microspectroscopes.

In addition, the present invention is not restricted to use within the film thickness measuring apparatus described above.

Although the present invention has been described and illustrated in detail, it is clearly understood that the same is by way of illustration and example only and is not to be taken by way of limitation. The spirit and scope of the present invention should be limited only by the terms of the appended claims.

What is claimed is:

1. A method of obtaining spectral data and calculating corrected spectra data, the method comprising the steps of:

obtaining spectral data $B'(\lambda)$ which is representative of the spectral characteristics of light which is generated by a light source and reflected by a standard sample;

substantially concurrently with the step of obtaining the spectral data $B'(\lambda)$, obtaining spectral data $R_0(\lambda)$ which is representative of the spectral characteristics of light which is generated by the light source;

after the step of obtaining the spectral data $B'(\lambda)$, obtaining spectral data $S'(\lambda)$ which is representative of the spectral characteristics of light which is generated by the light source and reflected by an object;

substantially concurrently with the step of obtaining the spectral data $S'(\lambda)$, obtaining spectral data $R(\lambda)$, which is representative of the spectral characteristics of light which is generated by the light source; and $\lambda$calculating corrected spectral data $S(\lambda)$ as a function of the spectra data $S'(\lambda)$, the spectral data $R(\lambda)$, the spectral data $B'(\lambda)$, the spectral data $R_0(\lambda)$ and known spectral data $B(\lambda)$ corresponding to the standard sample, the corrected spectral data $S(\lambda)$ being calculated as a function of:

$$\frac{R_0(\lambda) \cdot B(\lambda)}{R(\lambda) \cdot B'(\lambda)} \cdot S'(\lambda)$$

2. The method of claim 1, further comprising computing the thickness of the object based on the corrected spectral data $S(\lambda)$.

3. An optical system, comprising:
(A) a light source;
(B) a sample holder;
(C) reflecting means;
(D) a spectroscopic unit;
(E) a beam splitter for:
(1) transmitting light from said light source toward said sample holder and transmitting light reflected from said sample holder toward said spectroscopic unit so as to obtain spectral data which is representative of light reflected from said sample holder; and
(2) transmitting light from said light source toward said reflecting means and transmitting light reflected by said reflecting means toward said spectroscopic unit so as to obtain spectral data which is representative of light from said light source;

(F) a first shutter for selectively permitting and preventing the transmission of light between said beam splitter and said sample holder;

(G) a second shutter for selectively (1) permitting the transmission of light between said beam splitter and said reflecting means when said first shutter is preventing the transmission of light between said beam splitter and said sample holder and (2) preventing the transmission of light between said beam splitter and said reflecting means when said first shutter is permitting the transmission of light between said beam splitter and said sample holder; and (H) storage means for storing spectral data, and means for calculating corrected spectral data as a function of (1) spectral data stored in said storage means and (2) spectral data which is representative of the spectral characteristics of light which is generated by said light source and reflected by an object located at said sample holder.

4. An optical system, comprising:

(A) a light source;
(B) a sample holder;
(C) reflecting means;
(D) a spectroscopic unit;
(E) a beam splitter for:
  (1) transmitting light from said light source toward said sample holder and transmitting light reflected from said sample holder toward said spectroscopic unit so as to obtain spectral data which is representative of light reflected from said sample holder; and
  (2) transmitting light from said light source toward said reflecting means and transmitting light reflected by said reflecting means toward said spectroscopic unit so as to obtain spectral data which is representative of light from said light source; and (F) storage means for storing spectral data, and means for calculating corrected spectral data as a function of (1) spectral data stored in said storage means and (2) spectral data which is representative of the spectral characteristics of light which is generated by said light source and reflected by an object located at said sample holder;

wherein said reflecting means is a mirror, said mirror being selectively (1) positionable between said beam splitter and said sample holder and (2) removable to permit the transmission of light between said beam splitter and said sample holder.

5. An optical system, comprising:

(A) a light source;
(B) a sample holder;
(C) reflecting means;
(D) a spectroscopic unit;
(E) a beam splitter for:
  (1) transmitting light from said light source toward said sample holder and transmitting light reflected from said sample holder toward said spectroscopic unit so as to obtain spectral data which is representative of light reflected from said sample holder; and
  (2) transmitting light from said light source toward said reflecting means and transmitting light reflected by said reflecting means toward said spectroscopic unit so as to obtain spectral data which is representative of light from said light source;

(F) a first filter for restricting the transmission of light between said beam splitter and said sample holder;

(G) a second filter for restricting the transmission of light between said beam splitter and said reflecting means, said second filter being arranged with respect to said first filter such that said spectroscopic means is able to simultaneously obtain said spectral data which is representative of light from said sample holder and said spectral data which is representative of light from said reflecting means; and (H) storage means for storing spectral data, and means for calculating corrected spectral data as a function of (1) spectral data stored in said storage means and (2) spectral data which is representative of the spectral characteristics of light which is generated by said light source and reflected by an object located at said sample holder.

6. The system of claim 5, further comprising a first objective lens located between said beam splitter and said sample holder and a second objective lens located between said beam splitter and said standard sample, said objective lenses having substantially identical optical characteristics.

* * * * *